(12) United States Patent
Herz et al.

(10) Patent No.: US 8,839,658 B2
(45) Date of Patent: Sep. 23, 2014

(54) COMBINATION OF HYDROGEN AND PRESSURE SENSORS

(75) Inventors: Joshua J. Herz, Rochester, NY (US); David Billings, Spencerport, NY (US)

(73) Assignee: Qualitrol Company, LLC, Fairport, NY (US)

( * ) Notice: Subject to any disclaimer, the term of this patent is extended or adjusted under 35 U.S.C. 154(b) by 448 days.

(21) Appl. No.: 13/076,896

(22) Filed: Mar. 31, 2011

(65) Prior Publication Data

US 2012/0247185 A1 Oct. 4, 2012

(51) Int. Cl.
*G01N 7/00* (2006.01)
*G01N 33/28* (2006.01)

(52) U.S. Cl.
CPC .................. *G01N 33/2841* (2013.01)
USPC ....... 73/31.04; 73/19.1; 73/19.115; 73/19.05; 73/19.01

(58) Field of Classification Search
CPC ....... G01N 7/14; G01N 1/2294; G01N 33/24; G01N 33/2823; G01N 1/2226; G01N 2291/02433; G01N 33/18; G01N 33/2841; G01N 9/36; G01N 33/28; G01N 33/2888; G01N 7/10; G01N 7/00; G01N 7/16; D21H 19/00
USPC .......... 73/31, 49, 622, 23, 19.01, 19.1, 19.11, 73/19.05
See application file for complete search history.

(56) References Cited

U.S. PATENT DOCUMENTS

| | | |
|---|---|---|
| 3,559,457 A | 2/1971 | Collins |
| 3,921,440 A * | 11/1975 | Toth ................................. 73/622 |
| 3,927,555 A | 12/1975 | Godwin et al. |
| 4,112,737 A | 9/1978 | Morgan |

(Continued)

FOREIGN PATENT DOCUMENTS

| | | |
|---|---|---|
| EP | 1085635 A2 | 3/2001 |
| JP | 62-249045 A | 10/1987 |
| JP | 2004279063 A | 10/2004 |
| KR | 100811684 B1 | 3/2008 |

OTHER PUBLICATIONS

PCT—Notification of Transmittal of the International Search Report and the Written Opion of the International Searching Authority, or the Declaration; dated Nov. 1, 2012 (2 pages) (in International Patent Application No. PCT/US2012/030330).

(Continued)

*Primary Examiner* — Peter Macchiarolo
*Assistant Examiner* — Mohammed Keramet-Amircola
(74) *Attorney, Agent, or Firm* — Brian B. Shaw, Esq.; Thomas B. Ryan; Harter Secrest & Emery LLP

(57) ABSTRACT

The invention provides a sensor assembly for determining the concentration of hydrogen in an insulating fluid in electric power generation, transmission, and distribution equipment. The assembly includes a housing having an opening therein communicating with the fluid, a hydrogen sensor disposed in the housing and responsive to the concentration of hydrogen in the fluid and generating a signal related to the concentration of hydrogen, and a pressure sensor disposed in the housing responsive to the fluid and generating a second signal indicative of the pressure of the fluid in the equipment. The assembly further includes a signal processor disposed in the housing and connected to the hydrogen sensor and the pressure sensor and responsive to the first and second signals for generating a third signal representing the concentration of hydrogen in the fluid.

6 Claims, 4 Drawing Sheets

(56) References Cited

U.S. PATENT DOCUMENTS

| | | | |
|---|---|---|---|
| 4,271,474 A | | 6/1981 | Belanger et al. |
| 4,293,399 A | | 10/1981 | Belanger et al. |
| 4,654,806 A | | 3/1987 | Poyser et al. |
| 5,070,738 A | | 12/1991 | Morgan |
| 5,271,263 A | | 12/1993 | Gibeault |
| 5,659,126 A | | 8/1997 | Farber |
| 5,749,942 A | | 5/1998 | Mattis et al. |
| 5,773,709 A | | 6/1998 | Gibeault et al. |
| 5,937,893 A | * | 8/1999 | Herz ............................ 137/382 |
| 6,037,592 A | | 3/2000 | Sunshine et al. |
| 6,446,027 B1 | * | 9/2002 | O'Keeffe et al. ............. 702/183 |
| 6,906,630 B2 | | 6/2005 | Georges et al. |
| 7,228,725 B2 | | 6/2007 | Salter et al. |
| 7,249,490 B2 | | 7/2007 | Pendergrass |
| 7,268,662 B2 | | 9/2007 | Hines et al. |
| 7,471,208 B1 | * | 12/2008 | Hoben et al. .................. 340/622 |
| 7,565,827 B2 | | 7/2009 | Salter et al. |
| 7,747,417 B2 | | 6/2010 | Lamontagne |
| 2003/0029228 A1 | | 2/2003 | Bloder et al. |
| 2004/0261500 A1 | | 12/2004 | Ng et al. |
| 2005/0086998 A1 | * | 4/2005 | Qin ............................... 73/31.07 |
| 2005/0241382 A1 | | 11/2005 | Coenen |
| 2007/0068493 A1 | | 3/2007 | Pavlovsky |
| 2007/0125153 A1 | | 6/2007 | Visel et al. |
| 2007/0240491 A1 | | 10/2007 | Pavlovsky et al. |
| 2009/0301879 A1 | | 12/2009 | Soundarrajan et al. |
| 2010/0077828 A1 | | 4/2010 | Herz et al. |

OTHER PUBLICATIONS

PCT—International Search Report; dated Nov. 1, 2012 (3 pages) (in International Patent Application No. PCT/US2012/030330).

PCT—Written Opinion of the International Searching Authority; dated Nov. 1, 2012 (4 pages) (in International Patent Application No. PCT/US2012/030330).

PCT—Notification of Transmittal of the International Search Report and the Written Opinion of the International Searching Authority, or the Declaration; dated Mar. 11, 2010 (4 pages) (in International Patent Application No. PCT/US2009/054151).

PCT—International Search Report; dated Mar. 11, 2010 (3 pages) (in International Patent Application No. PCT/US2009/054151).

PCT—Written Opinion of the International Searching Authority; dated Mar. 11, 2010 (4 pages) (in International Patent Application No. PCT/US2009/054151).

Cargol, Tim, "An Overview of Online Oil Monitoring Technologies", Weidmann-ACTI, Inc., Fourth Annual Weidmann-ACTI Technical Conference, San Antonio, 2005, pp. 1-6.

Pavlovsky et al., "Palladium Nanoparticie Hydrogen Sensor", Gases & Technology Feature Jul./Aug. 2006, pp. 18-21.

Gas and Moisture Monitor GMM, Tree Tech Sistemas Digitais, CA-029, Jul. 20, 2006 Rev. 2, pp. 1-6.

Serveron, "Reliable energy through cost effective, on-line DGA", products and information (6 pages).

GE HydranMs Sensor, Technical Specifications, Appendix A, Part 16374, Rev. 2, Jul. 2005, A-1. pp. A1-A10.

Calisto, Dissolved Hydrogen and Water Monitor, Morgan Schaffer Systems, Transformers—The inside View (7 pages).

* cited by examiner

COMBINATION OF HYDROGEN AND PRESSURE SENSORS

CROSS-REFERENCE TO RELATED APPLICATIONS

None.

FIELD OF THE INVENTION

This invention relates to the sensing of hydrogen in oils. It particularly relates to apparatus for sensing of hydrogen in electric power generation transmission and distribution equipment oil.

BACKGROUND OF THE INVENTION

Electrical equipment, particularly medium-voltage or high-voltage electrical equipment, requires a high degree of electrical and thermal insulation between components thereof. Accordingly, it is well known to encapsulate components of electrical equipment, such as coils of a transformer, in a containment vessel and to fill the containment vessel with a fluid. The fluid facilitates dissipation of heat generated by the components and can be circulated through a heat exchanger to efficiently lower the operating temperature of the components. The fluid also serves as electrical insulation between components or to supplement other forms of insulation disposed around the components, such as cellulose paper or other insulating materials. Any fluid having the desired electrical and thermal properties can be used. Typically, electrical equipment is filled with an oil, such as castor oil, mineral oil, or vegetable oil, or a synthetic "oil", such as chlorinated diphenyl, silicone, or sulfur hexafluoride.

Often, electrical equipment is used in a mission-critical environment in which failure can be very expensive, or even catastrophic, because of a loss of electric power to critical systems. In addition, failure of electrical equipment ordinarily results in a great deal of damage to the equipment itself and surrounding equipment thus requiring replacement of expensive equipment. Further, such failure can cause injury to personnel due to electric shock, fire, or explosion. Therefore, it is desirable to monitor the status of electrical equipment to predict potential failure of the equipment through detection of incipient faults and to take remedial action through repair, replacement, or adjustment of operating conditions of the equipment. However, the performance and behavior of fluid-filled electrical equipment inherently degrades over time. Faults and incipient faults should be distinguished from normal and acceptable degradation.

A known method of monitoring the status of fluid-filled electrical equipment is to monitor various parameters of the fluid. For example, the temperature of the fluid and the total combustible gas (TCG) in the fluid is known to be indicative of the operating state of fluid-filled electrical equipment. Therefore, monitoring these parameters of the fluid can provide an indication of any incipient faults in the equipment. For example, it has been found that carbon monoxide and carbon dioxide increase in concentration with thermal aging and degradation of cellulosic insulation in electrical equipment. Hydrogen and various hydrocarbons (and derivatives thereof such as acetylene and ethylene) increase in concentration due to hot spots caused by circulating currents and dielectric breakdown such as corona and arcing. Concentrations of oxygen and nitrogen indicate the quality of the gas pressurizing system employed in large equipment, such as transformers. Accordingly, "dissolved gas analysis" (DGA) has become a well-accepted method of discerning incipient faults in fluid-filled electric equipment.

In conventional DGA methods, an amount of fluid is removed from the containment vessel of the equipment through a drain valve. The removed fluid is then subjected to testing for dissolved gas in a lab or by equipment in the field. This method of testing is referred to herein as "offline" DGA. Since the gases are generated by various known faults, such as degradation of insulation material or other portions of electric components in the equipment, turn-to-turn shorts in coils, overloading, loose connections, or the like, various diagnostic theories have been developed for correlating the quantities of various gases in fluid with particular faults in electrical equipment in which the fluid is contained. However, since conventional methods of off-line DGA require removal of fluid from the electric equipment, these methods do not, 1) yield localized position information relating to any fault in the equipment, 2) account for spatial variations of gases in the equipment, and 3) provide real time data relating to faults. If analysis is conducted off site, results may not be obtained for several hours. Incipient faults may develop into failure of the equipment over such a period of time.

The measurement of hydrogen gas in the oil of an electrical transformer is of interest as it is an indication of the breakdown of the oil caused by overheating and/or arcing inside the transformer. Transformer oil cools the transformer and acts as a dielectric. As transformer oil ages it becomes a less effective dielectric. The increase in hydrogen dissolved in the transformer oil is an indicator of the coming failure of the transformer.

For large transformers there are hydrogen sensors that use gas chromatography or photo-acoustic spectroscopy to determine the amount of hydrogen gas within a transformer's oil. Such devices are very expensive and the expense is not justified for smaller transformers. There are many older, small transformers that could be monitored if a low-cost method of doing so was available.

A lower-cost gas monitor, the Hydran™ M2 manufactured by General Electric Company has been in use. However, this gas monitor only senses combustible gases and then uses a formula to estimate how much of the gas typically is hydrogen and how much is other gases.

An article "Overview of Online Oil Monitoring Technologies" by Tim Cargol at the Fourth Annual Weidmann-ACTI Technical Conference, San Antonio 2005 provides a discussion of oil gas measuring techniques, including hydrogen measurement.

Palladium hydrogen sensors are disclosed in Gases and Technology, July/August 2006, in the article, "Palladium Nanoparticle Hydrogen Sensor" pages 18-21. Palladium sensors are also disclosed in U.S. Patent Publications 2007/0125153-Visel et al., 2007/0068493-Pavlovsky, and 2004/0261500-Ng et al. U.S. Patent Application No. 2010/007828 discloses a hydrogen sensor for an electrical transformer.

There is a need for low-cost method of determining hydrogen gas content in oils, such as in electric power generation and transmission and distribution equipment especially transformers. There is a particular need for a method and apparatus for mounting a hydrogen sensor to electric power generation transmission and distribution equipment that does not require taking the equipment out of service and preferably uses existing fittings or ports in the equipment without the necessity of making new openings in the housings for the equipment. It would particularly advantageous to provide a method and apparatus for attaching a hydrogen sensor to a transformer or the like using the port used for a pressure sensor especially a rapid pressure rise sensor.

BRIEF SUMMARY OF THE INVENTION

The invention provides a sensor assembly for determining the concentration of hydrogen in an insulating fluid in electric power generation, transmission, and distribution equipment. The assembly includes a housing having an opening therein communicating with the fluid, a hydrogen sensor disposed in the housing and responsive to the concentration of hydrogen in the fluid and generating a signal related to the concentration of hydrogen, and a pressure sensor disposed in the housing responsive to the fluid and generating a second signal indicative of the pressure of the fluid in the equipment. The assembly further includes a signal processor disposed in the housing and connected to the hydrogen sensor and the pressure sensor and responsive to the first and second signals for generating a third signal representing the concentration of hydrogen in the fluid.

DETAILED DESCRIPTION OF THE INVENTION

The invention provides numerous advantages over prior apparatus. The invention is smaller, easily installed, and lower in cost than other hydrogen sensing devices. The device is accurate and can be easily retrofitted onto existing transformers or engines. The device provides a very accurate hydrogen sensor with real time results as removal of fluid is not required. The device allows replacement of the sensor without providing a significant opening for oil to leave the container. The invention sensor utilizes instrument controls that are well known and available. These and other advantages will be apparent from the description below.

The invention provides easy retrofit of the hydrogen sensor to the transformer as an opening in the transformer housing is already present. This also is lower in cost than if a new inlet to the transformer needed to be installed. Further, the installation of the invention is low maintenance and will work at higher temperatures such as 120° C.

Figure 1:
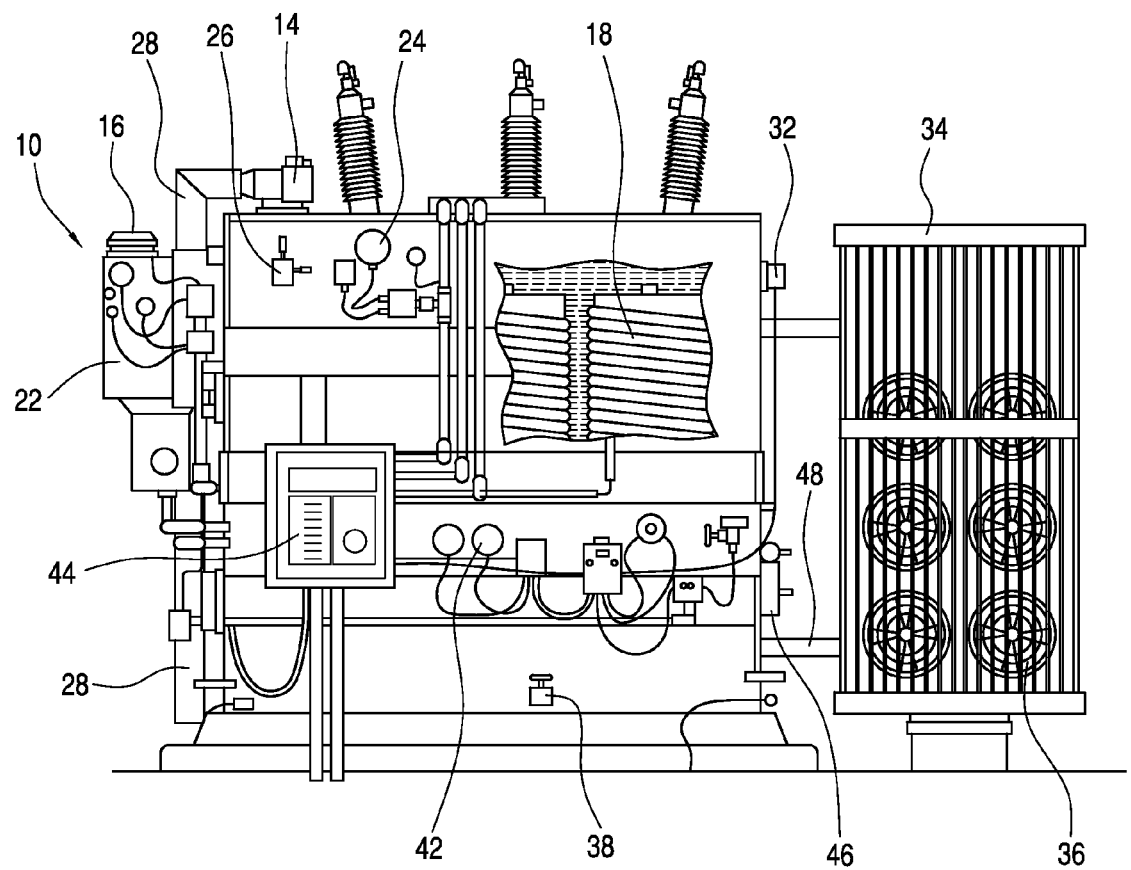
FIG. 1 is a view of a transformer indicating possible locations for the attachments for sensors.

Illustrated in FIG. 1 is a transformer 10. The transformer 10 is provided with pressure relief devices 14 and 16. The transformer 10 is partially cutaway to show the coils 18. The transformer 10 has a temperature gauge 24. The temperature gauge 26 measures the temperature of the oil of the transformer. The pipe terminal 28 connects to the overflow pipe leading from pressure relief device 14. The optical fiber entry 32 provides direct reading of the winding temperature. A cooling tower 34 is utilized to regulate the temperature of the oil in the transformer by cooling when necessary using fans 36. The drain valve 38 is utilized to drain the oil for changing or to secure test samples. Electromechanical thermometers 42 sense the temperature of the oil in the transformer. The IED intelligent electronic device 44 controls the sensing devices and provides readouts of the information sensed. It further may control the cooling of the reactor as necessary. A rapid pressure rise relay 46 is also provided on the transformer. A flow gauge, not shown may be provided at location 48. The various temperature and pressure sensors, pressure release devices, drains, and flow gauges may provide mounting areas for hydrogen sensors.

Figure 2:
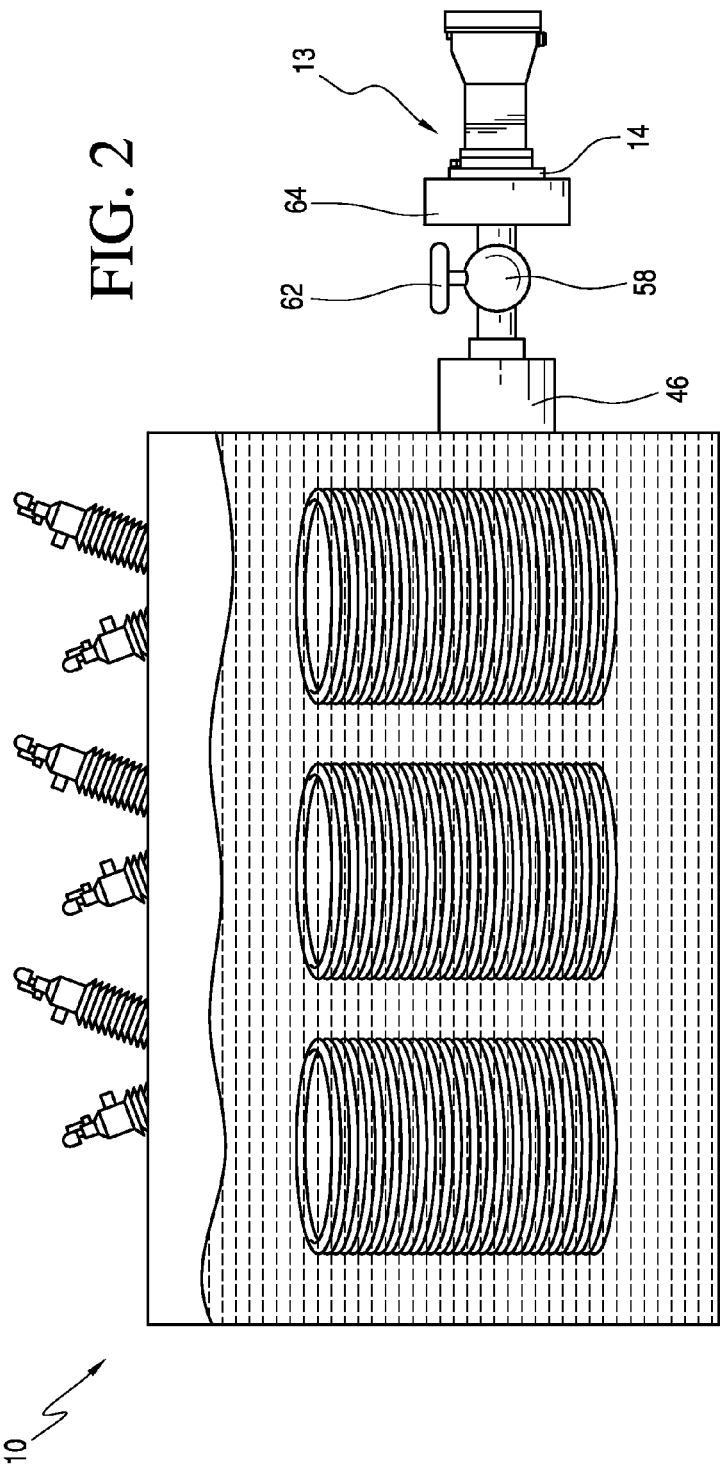
FIG. 2 is a view of a transformer indicating a location on the transformer.
Figure 3:
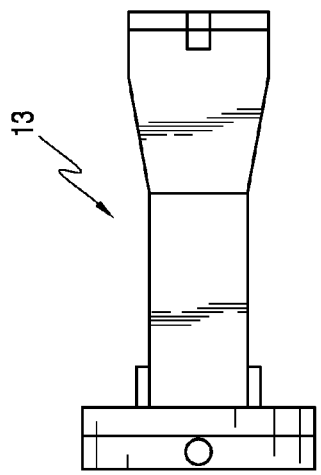
FIG. 3 is a top view of the sensor housing shown in FIG. 2.

FIG. 2 shows a transformer 10 having a hydrogen sensor housing 13 mounted on flange 46 of the transformer 10. The housing 13 is attached to the flange 46 by way of shutoff valve 58. The valve may be turned off by knob 62. FIG. 3 is a top view of the hydrogen sensor housing 13.

Figure 4:
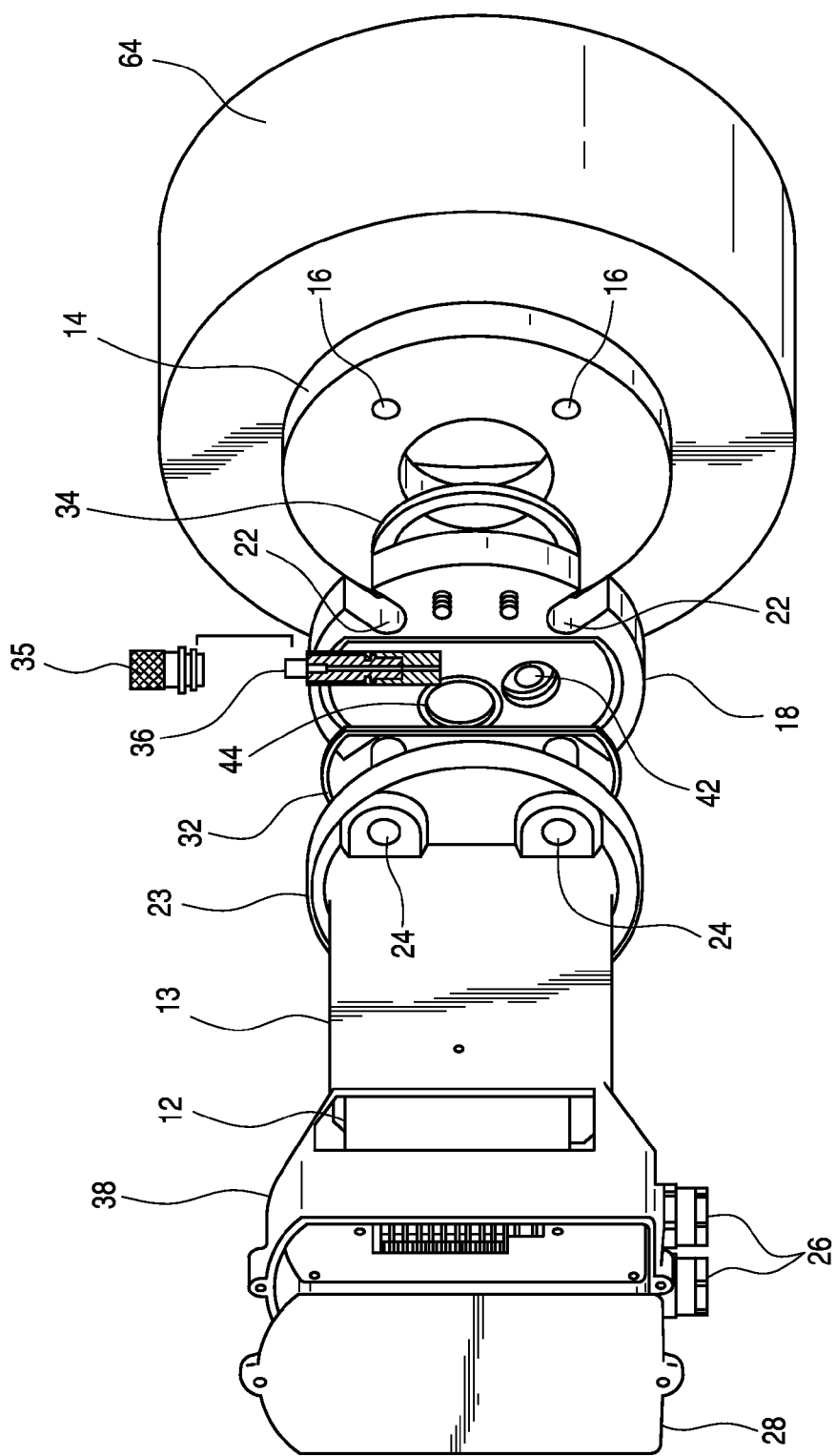
FIG. 4 is a prospective view of the housing for sensors.

FIG. 4 is an exploded perspective illustration of the housing 13 as mounted onto a transformer, by way of a shutoff valve 58. The flange 64 provides access to the transformer through the shut off valve 58. As illustrated in FIG. 4 the sensors are not present. The housing element 13 contains a semiconductor element 12 for measuring hydrogen concentration in an insulating fluid in electric power generation transmission and distribution equipment. The mounting flange 14 has a plurality of bolt holes 16 and provides access to the interior of the transformer equipment and provides a plurality of bolt receiving openings 16 arranged on the mounting flange 14 in a first pattern. The first flange 18 has one or more openings for receiving one or more semiconductor hydrogen sensors and an outside periphery. The first flange is also provided with a plurality of bolt receiving apertures (not shown) that correspond to the bolt pattern 16 of the mounting flange 14. A second flange 23 having a second plurality of bolt receiving apertures corresponding to the first pattern and the bolt holes within the periphery of the second flange is provided as the end of the housing element 13. The housing body 13 has the bolt apertures in the second flange 23 disposed a sufficient distance from the housing to allow access for bolts (not shown) to be disposed in the apertures for inserting and removing the bolts from the apertures and the second flange has an outer periphery contained within the outer periphery of the first flange.

The housing is provided with at least one wire receiving opening 26 extending from the housing body 13 at the expanded end 38. A cover 28 is provided for closing the end of the housing body distal from the mounting second flange 23. The first seal 32 is disposed between the first and second flanges. The first seal provides sealing around the one or more sensor receiving openings 42 and 44 and the valve opening of the sampling or bleeding valve 36. A second seal 32 is disposed on the first flange for engaging the mounting flange. The second seal surrounds and seals the sensor receiving openings 42 and 44 when sensors are inserted. A sampling or bleeding valve 36 is disposed on the first flange in communication with the interior of the equipment and oriented so that when opened trapped gas will exit the valve. A cap 35 for the valve 36 is provided. The sampling valve extends to an edge of the flange 18 and communicates with the inner surface of the flange opposite the housing body.

The housing 13 comprises an expanded end 38 on the end opposite to the second flange. It is noted that sensor opening 44 is generally in the center of and perpendicular to the first flange. The second opening 42 is somewhat to the side and is threaded at an oblique angle to the flange to provide more clearance for the second sensor. The oblique angle also permits any trapped air to move from the tip of the pressure sensor to the bleed valve.

Figure 5:
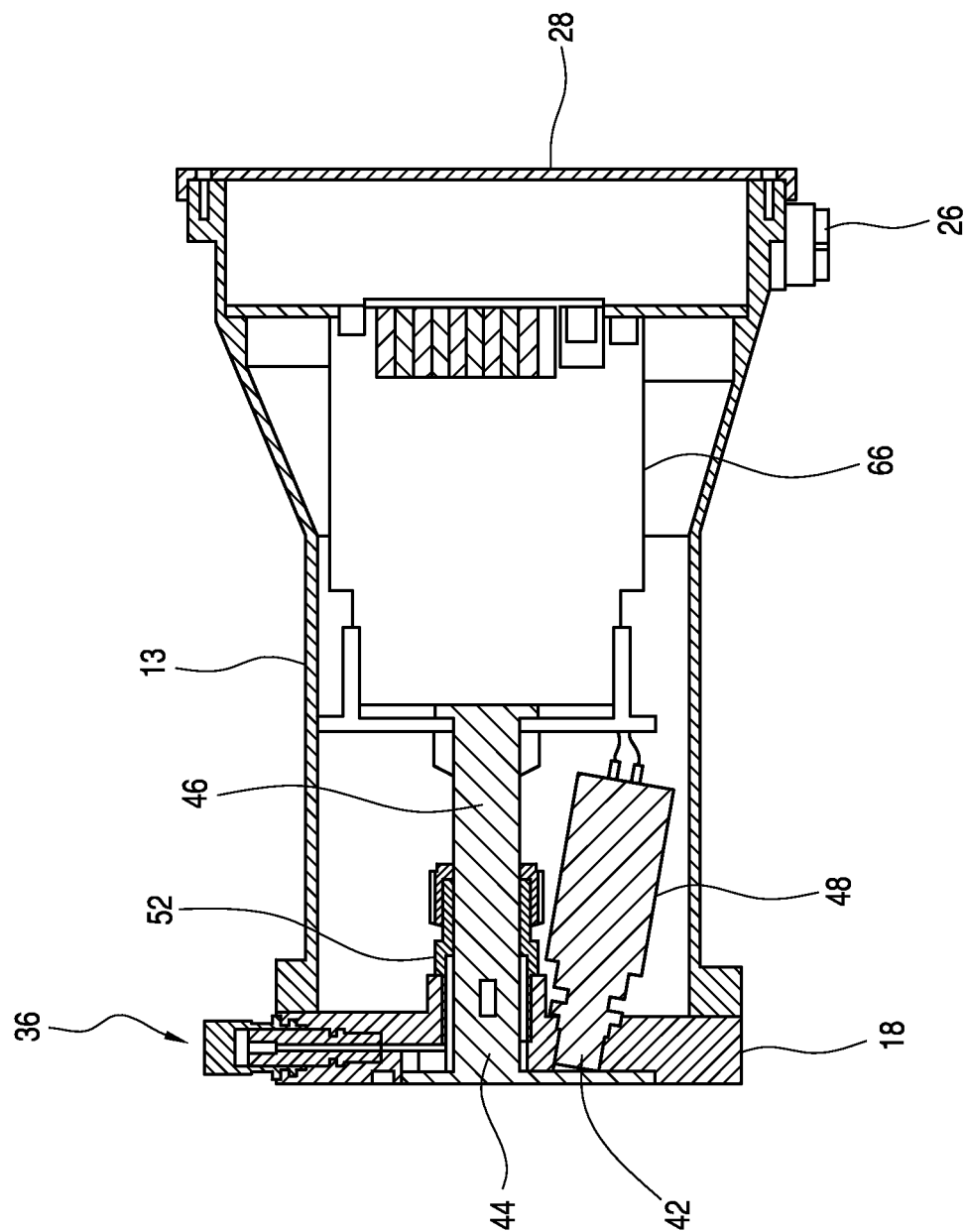
FIG. 5 is a cross-section of the invention housing with sensors installed.

FIG. 5 shows the sensor assembly with a detector 46 for hydrogen in insulating fluid in electric power generation, transmission, and distribution equipment installed in a housing such as in FIG. 4. The hydrogen sensor is responsive to the concentration of hydrogen in the fluid and generates a signal related to the concentration of hydrogen. A pressure sensor 28 is also disposed in the housing and is responsive to the fluid and generates a second signal indicative of the pressure of the fluid in the equipment. A signal processor 66 is in the housing and connected to the hydrogen sensor, and the pressure sensor. The signal processor 66 is responsive to the first and second signals for generating a third signal representing the concentration of hydrogen in the fluid.

The sensor assembly comprises a tube 52 threaded into the threaded opening 44 of the first flange 18. The hydrogen sensor 46 is disposed in the tube 52. The second threaded opening 42 has a pressure sensor 48 threaded into the opening 42.

The sensor assembly and housing that accepts two sensors is particularly desirable as two sensors are placed onto one flange of the transformer, power generator other electrical equipment. Generally, in sensing hydrogen in a gas there is a need to know the gas pressure of the fluid in order to do a known calculation to determine the percentage of hydrogen present. If the hydrogen sensor is in oil, pressure is not needed to calculate hydrogen content of the oil. The placement of two sensors in one housing on one flange is a compact method of obtaining two measurements. While illustrated with the hydrogen composition calculation being done in the sensor housing it is also possible that the IED central control unit could do the calculation and provide the reading. Having the hydrogen sensor immediately adjacent the pressure sensor allows better accuracy than if the two sensors are in the air space.

The entire unit can also be used in the gas space in sealed transformers, not just under oil, and it is where the pressure measurement is in the gas space that the pressure sensor, in combination with the hydrogen sensor, would do double duty to allow calculation of hydrogen concentration as well as measure rapid pressure rise.

As is apparent from the drawings the placement of the first flange 64, between the mounting flange 14 of the shut off valve 58 allows placement of the oxygen sensor without the formation of an additional hole in the transformer. The location of the rapid pressure release device 46 at the side of the transformer allows sampling of hydrogen in the transformer oil rather than in the open space above the liquid coolant. Other locations also would place the hydrogen sensor in the liquid coolant. Sensors are known for sensing hydrogen in liquid as well as in gas and selection of the proper sensor would be within the skill of the art depending upon what type of transformer is utilized and the level of the transformer oil. It is noted that for accurate sensing of the hydrogen content oil or gas that the pressure of the oil or gas also needs to be sensed.

The sampling valve 36 extends through an edge of the first flange 18 and communicates with a surface of the flange opposite the housing body and communicates with an opening exposed to the interior of the transformer equipment through the mounting flange 64.

Palladium containing hydrogen sensors and controllers for the sensors are known in the art. Such sensors are disclosed in United States Patent Publication Nos. 2007/0125153-Visel et al. and 2007/0240491-Pavlovsky, hereby incorporated by reference. An article in Gases and Technology, July/August 2006 "Palladium Nanoparticle Hydrogen Sensor" by I. Pavlovsky, also contains a description of hydrogen sensors and the methods and apparatus for their use. The palladium nanoparticles utilized in these preferred sensors for the invention are intrinsically sensitive to hydrogen and sensors based on palladium nanoparticle networks do not produce false alarms in the presence of other gases. This makes them particularly desirable for use in the devices of the invention as other gases may be present when the hydrogen is sensed. Other hydrogen sensors and their controllers are disclosed in U.S. Patent Publication Nos. 2007/0068493-Pavlovsky and 2007/0240491-Pavlosky et al., also incorporated herein by reference. The preferred hydrogen sensor for the instant invention is a semiconductor palladium-type sensor because it provides good performance in the transformer environment.

While the drawings illustrate the attachment of the hydrogen, sensing device to the rapid pressure release device this mounting method could be utilized at other locations on the transformer where there is a flange opening and space for the hydrogen sensor. Other locations to consider would be on the load tap changer 22 and the drain valve 38.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A sensor assembly for determining the concentration of hydrogen in an insulating fluid in electric power generation, transmission, and distribution equipment comprising:
 (a) a housing having an opening therein communicating with the fluid;
 (b) a hydrogen sensor disposed in the housing and responsive to the concentration of hydrogen in the fluid and generating a signal related to the concentration of hydrogen;
 (c) a pressure sensor disposed in the housing responsive to the fluid and generating a second signal indicative of the pressure of the fluid in the equipment; and;
 (d) a signal processor disposed in the housing and connected to the hydrogen sensor and the pressure sensor and responsive to the first and second signals for generating a third signal representing the concentration of hydrogen in the fluid, wherein the housing comprises a flange having a first threaded opening therethrough, a tube threaded into the opening, and in which the hydrogen sensor is disposed in the tube.

2. The sensor assemble of claim 1, comprising a second threaded opening in the flange.

3. The sensor assembly of claim 2, in which the pressure sensor is threaded into the second opening.

4. The sensor assembly of claim 1, comprising a sampling valve extending through the housing in communication with the insulating fluid.

5. The sensor assembly of claim 4, in which the sampling valve extends through a sidewall of the flange.

6. The sensor assembly of claim 5, in which the sampling valve communicates with a valve opening exposed to the interior of the equipment.

\* \* \* \* \*